United States Patent [19]
Knoll

[11] Patent Number: 5,413,591
[45] Date of Patent: May 9, 1995

[54] CURRENT TRUNCATED WAVEFORM DEFIBRILLATOR

[75] Inventor: Mark W. Knoll, Minnetonka, Minn.

[73] Assignee: Angeion Corporation, Plymouth, Minn.

[21] Appl. No.: 96,009

[22] Filed: Jul. 22, 1993

Related U.S. Application Data

[63] Continuation-in-part of Ser. No. 841,544, Feb. 26, 1992, Pat. No. 5,306,291.

[51] Int. Cl.$^6$ .............................................. A61N 1/362
[52] U.S. Cl. ....................................................... 607/6
[58] Field of Search ........................... 607/5, 6, 7, 8, 28

[56] References Cited

U.S. PATENT DOCUMENTS

| | | |
|---|---|---|
| 3,942,536 | 3/1976 | Mirowski et al. |
| 4,499,907 | 2/1985 | Kallok et al. |
| 4,800,883 | 1/1989 | Winstrom |
| 4,811,156 | 3/1989 | Kroll |
| 4,964,406 | 10/1990 | Carroll et al. |
| 4,969,463 | 11/1990 | Dahl et al. |
| 5,007,422 | 4/1991 | Pless |
| 5,083,562 | 1/1992 | Coriolis et al. |

FOREIGN PATENT DOCUMENTS 020892 10/1993 WIPO ........................................ 607/5

OTHER PUBLICATIONS

Improved Defibrillator Waveform Safety Factor with Biolastic Waveforms by Jones et al., Am. J. Physiol. 245 (Heart Circ. Physiol. 14): H60–H65, 1983.

Yabe et al., Circulation Research, 66:1190–1203, 1990.

Barker–Voelz et al., J. Electrocardiology, 16(2): 167–180, 1983.

Schwartzman, D. et al., Pacing and Clinical Electrophysiology the NASPE Abstracts, 16(4):Part II, p. 916 #263, 1993.

Chapman et al., Am. Heart J., 114, 274, 1987.

J. L. Prevost and F. Batelli, "Sur quelques effets des descharges electriques sur le couer des mammifers", Compies rendus hebdomadaires des seances de l'Academie des sciences, vol. 129, p. 1267, 1899.

R. A. Winkle, R. H. Mead, M. A. Ruder, et al., "Long-term outcome with the implantable cardioverter-defibrillator", J Am Coll Cardiol., vol. 13, p. 1353, 1989.

M. H. Lehman, S. Saksena, "Implantable cardioverter-defibrillators in cardiovascular practice: Report of the policy conference of the North American Society of Pacing and Electrophysiology", PACE, vol. 14, pp. 969–979, Jun. 1991.

J. N. Wetherbee, et al., "Sequential Shocks are Comparable to Single Shocke Employing Two Current Pathways for Internal Defibrillation in Dogs", PACE, vol. 11, p. 696, Jun., 1988.

J. N. Wetherbee, et al., "Nonthroctomy Internal Defibrillation in Dogs: Threshold Reduction Using a Subcutaneous Chest Wall Electrode with a Transvenous Catheter Electrode", J. Am. Coll. Cardiol., vol. 10, p. 406, Aug. 1987.

J. C. Schuder, H. Stoeckle, J. A. Wes, et al, "Transthoracic ventricular defibrillation in the dog with truncated and untruncated exponential stimuli", IEEE Trans. Biom. Eng., vol. BME–18 #6, pp. 410–415, Nov. 1971.

G. Weiss, "Sur la possibilite' de rendre comparable entre eux les appareils survant a l'excitation electrique", Arch. Ital. de Biol., vol. 35, pp. 413–446, 1901.

(List continued on next page.)

Primary Examiner—William E. Kamm
Assistant Examiner—Scott M. Getzow
Attorney, Agent, or Firm—Patterson & Keough

[57] ABSTRACT

A system and method is provided for implantable cardioverter defibrillators to truncate peak current output during defibrillation countershock therapy to a safe level irrespective of the resistance of the myocardium between the discharge electrodes implanted within the heart.

16 Claims, 5 Drawing Sheets

OTHER PUBLICATIONS

L. Lapicque, "Definition experimentalle de l'excitabilite'", *Proc. Soc. de Biol.*, vol. 77, pp. 280–285, 1909.

A. C. Guyton and J. Satterfied, "Factors concerned in defibrillation of the heart, particularly through the unopened chest", *Am J. of Physiology*, vol. 167, pp. 81, 1951.

J. C. Schuder, G. A. Rahmoeller, and H. Stoeckle, "Transthoracic ventricular defibrillation with triangular and trapezoidal waveforms", *Circ Res*, vol. 19, pp. 689–694, Oct. 1966.

W. A. Tacker, L. A. Geddes, J. McFarlane, et al., "Optimum current duration for capacitor–discharge defibrillation of canine ventricles", *J Applied Physiology*, vol. 27 #4, pp. 480–483, Oct. 1969.

R. A. Winkle, "State-of-the-Art of the AICD", *PACE* vol. 14, pp. 961–966, May 1991, pt. II.

N. G. Tullo, S. Saksena, R. B. Krol, "Technological improvements in future implantable defibrillators", *CARDIO*, vol. , pp. 107–111, May 1990.

D. P. Zipes, J. Fischer, R. M. King, et al, "Termination of venticular fibrillation in dogs by depolarizing a critical amount of myocardium", *Am J Cardiol.*, vol. 36, pp. 37–44, Jul. 1975.

CURRENT TRUNCATED WAVEFORM DEFIBRILLATOR

RELATED APPLICATION

This application is a continuation-in-part of an application filed in the United States Patent and Trademark Office on Feb. 26, 1992, entitled OPTIMAL ENERGY STEERING FOR AN IMPLANTABLE DEFIBRILLATOR, Ser. No. 07/841,544 now U.S. Pat. No. 5,306,291, which is also assigned to the assignee of the present invention, a copy is attached and hereby incorporated in the present application.

BACKGROUND

1. Field of the Invention

The present invention relates generally to cardiac defibrillators, and in particular to modification of the current waveform applied to the myocardium by truncating the peak initial current during defibrillation countershock therapy when excessively low myocardial tissue resistance will lead to myocardial tissue destruction.

2. Background of the Invention

The last several decades have seen considerable advancement in the treatment of cardiac dysrhythmias. Particularly dramatic results have been achieved in the treatment for ventricular fibrillation. Early defibrillation systems were externally applied and, as the efficacy of the system was proven, efforts focused on providing increasingly smaller defibrillation systems that would be suitable for implantation. Examples of such automatic implantable defibrillator systems include U.S. Pat. No. 4,800,883 issued to Winstrom, and U.S. Pat. No. 5,007,422 isued to Pless et al. As these implantable automatic defibrillator systems continue to be improved, one challenge is to provide adequate energy output from the battery and capacitors of the system, while decreasing the overall size of the implanted defibrillator system. Another challenge is to provide the energy output in a reasonably safe fashion.

Experience has shown that the needed energy output of existing implantable defibrillator systems is in the range of 25–40 Joules (J) over approximately a six milliseconds (msec) period to insure consistently successful defibrillation. Contrast this to the 200–400 J of output energy necessary for the skin to skin externally applied defibrillation countershocks.

Existing implantable defibrillator systems generally accumulate the output energy in a storage capacitor system having an effective capacitance of approximately 150 microfarads ($\mu$F) charged to 750 volts (V) and delivering the output energy as a defibrillation countershock pulse over approximately a six msec period through approximately 50 $\Omega$ of myocardial muscle resistance between two or more implantable discharge electrodes. For a general background on implantable cardioverter defibrillators (ICD) and cardioversion defibrillation therapies, reference is made to: *Implantable Cardioverter Defibrillator Therapy: The Engineering-Clinical Interface*, (M. W. Kroll, Ph.D., M. H. Lehmann, M.D. editors 1993).

Early defibrillator systems delivered a defibrillation countershock pulse as a mono-phasic waveform. Further development and research revealed that for treatment of ventricular fibrillation, a bi-phasic waveform is a more efficacious shape for a defibrillation countershock pulse. For further background on the efficacy of waveform shape, reference is made to: "Improved defibrillator waveform safety factor with bi-phasic waveforms" by Jones et al. in *Am. J. Physiol.* 245 (*Heart Circ. Physiol.* 14): H60–H65, 1983; and "Conduction Disturbances Caused by High Current Density Electric Fields" by Yabe et al. in *Circulation Research* 66: 1190–1203, 1990.

On the average, myocardial tissue resistance between any two implanted discharge electrodes has been found to be 50 ohms ($\Omega$) and this has become the accepted average resistance of the myocardial tissue between the discharge electrodes for implantable systems. At the time of implantation, the physician will test this resistance to assess adequacy of electrode placement. If the myocardial tissue resistance between the discharge electrodes is too high then the system will not deliver enough energy to insure consistent success in defibrillating. If the myocardial tissue resistance is too low, initial peak currents will be excessive in the local area of the discharge electrodes causing temporary to permanent tissue injury to an already ailing heart.

Physician experience with implantable defibrillator systems has demonstrated that ideal patient conditions are not always encountered. Placement of electrodes in positions that will include the vast majority of the myocardium within the electrical discharge field and will not encounter adverse physical conditions is difficult to achieve in some patients. One of the primary adverse physical conditions encountered during implantation of a defibrillator system is too low of a load resistance between electrodes. Low inter-electrode resistance can cause unacceptably high peak current during delivery of a defibrillation countershock pulse that leads to tissue destruction in the heart in a zone beginning from the center of the electrical field and extending outward. An additional problem caused by high peak currents in the defibrillation countershock pulse is tissue stunning extending radially outward from the border of the destruction zone for some additional distance. For additional background on this type of high current tissue destruction, reference is made to: "Alterations Induced by a Single Defibrillation Shock Applied through a Chronically Implanted Catheter Electrode" by Barker-Voelz et al. in *J. Electrocardiology* 16(2): 167–180, 1983.

After implantation the myocardial tissue resistance can and does change. In addition to high peak current problems encountered during implantation, high peak current problems can also develop after the device has been implanted. Unfortunately, the system is now enclosed within the patient and if the resistance drops dangerously low, there is currently no way to detect this change. For additional background on fluctuating interelectrode myocardial tissue resistance, reference is made to the following abstract: "Serial Patch-Patch Impedance Values In An Epicardial Defibrillation System," by David Schwartzman, M.D., et. al. in *Pacing And Clinical Electrophysiology*, the NASPE Abstracts, 16(4): Part II; page 916, abstract number 263, April 1993.

Existing approaches to minimize the problems associated with high peak currents involve a decrease in the high peak current by decreasing the charging voltage used to charge the capacitors of the defibrillator system. If low inter-electrode resistance is encountered by a physician during implantation of a defibrillator system, the recommended course of action is to programmably decrease the initial charging voltage which the system uses to deliver a defibrillation countershock pulse through electrodes having a low inter-electrode resistance.

The disadvantage to this technique is that the maximum total output energy of the defibrillator system is compromised by decreasing the initial charging voltage. Unfortunately, the total output energy of a defibrillation countershock pulse is directly related to the efficacy of the defibrillator system. Therefore, decreasing the charging voltage in an attempt to avoid tissue destruction increases the likelihood of encountering treatment failure. For further background on the relationship between output energy and efficacy of the defibrillation countershock pulse, reference is made to: "Relationship of left ventricular mass to defibrillation threshold for the implantable defibrillator: A combined clinical and animal study" by Chapman et al. in *Am. Heart J.* 114: 274, 1987.

A general review of the art in the biomedical use of current limiting has revealed the following references. U.S. Pat. No. 4,811,156 issued to Kroll discloses a current limiting apparatus for use in medical monitoring devices that is designed to protect the patent from transient or spurious currents that could possibly shock the patient. The invention of the Kroll patent limits current in an implanted device to about 5 microamps as a safety maneuver to prevent shocks. Thus, by its very nature to prevent shocks, the invention of the Kroll patent is plainly not suited for use with an implantable cardioverter defibrillator which is specifically designed to deliver shocks.

In U.S. Pat. No. 5,083,562 issued to de Coriolis et al., discloses a current limiting mechanism designed to protect a semiconducting switch which uses a small capacitor from inadvertent switch activation by spurious electro-surgery or electro-cautery currents. However, the current limiting circuitry required to exclude spurious electro-surgery or electrocautery currents in the de Coriolis et al. patent simply can not be applied to the output current across the defibrillator electrodes.

U.S. Pat. No. 4,499,907 issued to Kallok et al., discloses a transvenous catheter capable of limiting the energy that the catheter would provide to the discharge electrodes at its tip. The purpose of the catheter is to be able to couple an external defibrillating system to a catheter that has been implanted through a transvenous route. External defibrillator systems provide upwards of 360 joules of energy with the intent to deliver this amount of energy through externally applied large surface area paddle electrodes at the skin interface. Electrodes applied directly to the epicardium or within the heart chambers via transvenous routes as used with implantable systems successfully defibrillate the heart with as little as or less than 40 joules of energy. Consequently, in order to adapt an external defibrillator system for intravenous use, some mechanism must be in place to limit the energy output to less than 40 joules of energy. The transvenous catheter disclosed by Kallok et al., discloses a lossy element in series with one discharge electrode and a second lossy element in parallel to the myocardium that allows for shunting of approximately 90% of the energy. Thus, the Kallok et al., invention always limits the amount of energy delivered to the discharge electrodes to 10% of the energy applied. Furthermore, the case of a physically large lossy element would preclude the use of the current limiter of Kallok et al., for implantable cardioverter defibrillators.

Finally, U.S. Pat. No. 4,969,463 to Dahl et al., teaches a device and method to overcome current limiting effects of defibrillation countershock. Dahl et al., teach the concept that high energy defibrillation creates gas formation secondary to electrolysis at the surface of the electrode sites. Formation of this gas on the surfaces increases resistance which decreases the amount of energy the defibrillation system can deliver. In order to overcome the increased resistance and current and voltage limiting effects due to electrolysis, Dahl et al., teaches a sequential gatling type electrical discharge through a series of small electrodes.

While significant improvements have been made to existing automatic implantable defibrillator systems, such systems are presently designed to operate with discharge electrodes that assume ideal physical conditions of the patient in whom the system will be implanted. In the event that a physician encounters a less than ideal electrode placement during implantation of the defibrillator system, existing techniques necessarily compromise the efficacy of the system in order to compensate for low interelectrode resistance. Accordingly, it would be advantageous to provide a technique for use with automatic implantable defibrillator systems that compensates for low inter-electrode resistance without decreasing the efficacy of the defibrillation countershock pulses.

SUMMARY OF THE INVENTION

According to the present invention, a current truncation system and related method is provided for use in conjunction with automatic implantable cardioverter defibrillators. The current truncation system is preferably a non-linear output current truncater electrically connected in series with an appropriate power supply source and discharge electrodes. Such a system truncates peak current discharge through the discharge electrodes irrespective of the resistance of the myocardium between the electrodes.

Unlike existing devices, the present invention can accommodate changes in myocardial resistance that may occur after implantation. In existing systems, if the resistance drops at some time after implantation and the drop goes undetected, the patient is at risk of receiving an inordinately large peak current when that system delivers a defibrillation countershock. In the present invention, the current truncation system is designed in such a way as to truncate current in the upper end of the countershock modalities, particularly defibrillation countershocks. Cardioversion and pacing countershocks utilize significantly less total energy output and, therefore, usually do not require current truncation. Accordingly, the present invention does not interfere with or truncate current output during these therapy modalities.

An additional advantage of the present invention is that greater voltage and current are provided to the second phase of a bi-phasic defibrillation countershock pulse when low inter-electrode resistance is encountered, thus increasing the efficacy of membrane healing and avoiding detrimental low trailing voltages in the second half of a bi-phasic defibrillation countershock pulse.

An object of the present invention is to provide a circuit system and method for an automatic implantable cardioverter defibrillator that is capable of non-linear current truncation, thereby truncating initial peak current outputs of an implantable cardioverter defibrillator while responding to the detection of various heart disorders and arrhythmias.

Another objective of the present invention is to provide a system and method truncating peak cardioverter defibrillator discharge currents thereby decreasing the problems associated with local myocardial damage and stunning.

A further objective of the present invention is to provide a system and method for truncating current output that is restricted to the defibrillation therapeutic range.

Another further objective of the present invention is to provide a system and method that truncates peak current output of defibrillation countershocks to safer levels without having to decrease charging voltage when low inter-electrode resistance is encountered either at time of implantation or after implantation during the lifetime of the device.

DETAILED DESCRIPTION OF THE PREFERRED EMBODIMENT

Figure 1:
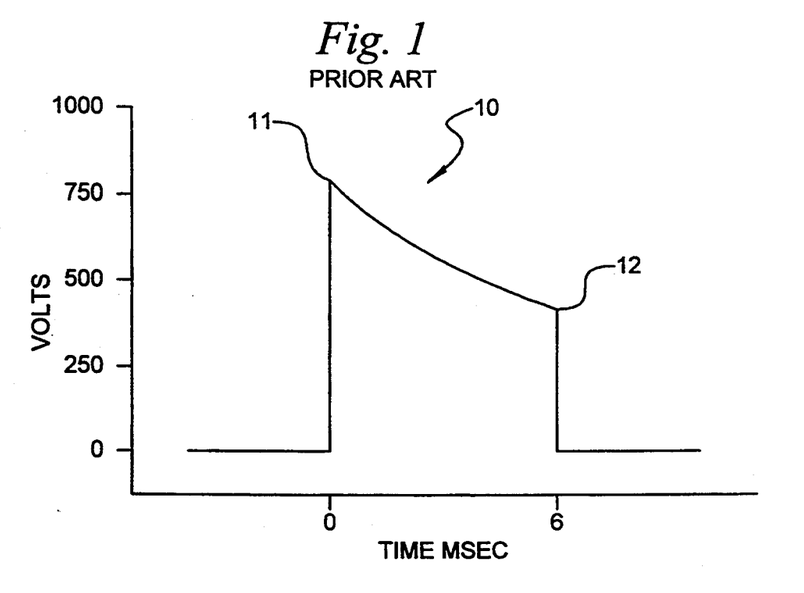
FIG. 1 is a graphic depiction of the monophasic voltage output of a typical prior art implantable cardioverter defibrillator system.

FIG. 1 depicts a conventional mono-phasic defibrillation countershock 10 through an assumed 50 $\Omega$ inter-electrode myocardial muscle resistance by delivering the charge from a 150 $\mu$F capacitance charged to 750 V. Using Ohm's Law of $I = V/R$, then where leading edge voltage 10 is 750 V, Ohm's Law provides a peak initial instantaneous current of 15 amps (A). Trailing edge voltage 12 is 337 V at the time of truncation six milliseconds (msec) later. Total energy delivered during this six msec pulse period is 33.6 J as given by the equation $J = \frac{1}{2}(CV^2)$. Experience has shown that the technique of time truncation significantly increases the efficacy of the defibrillation countershock.

Figure 2:
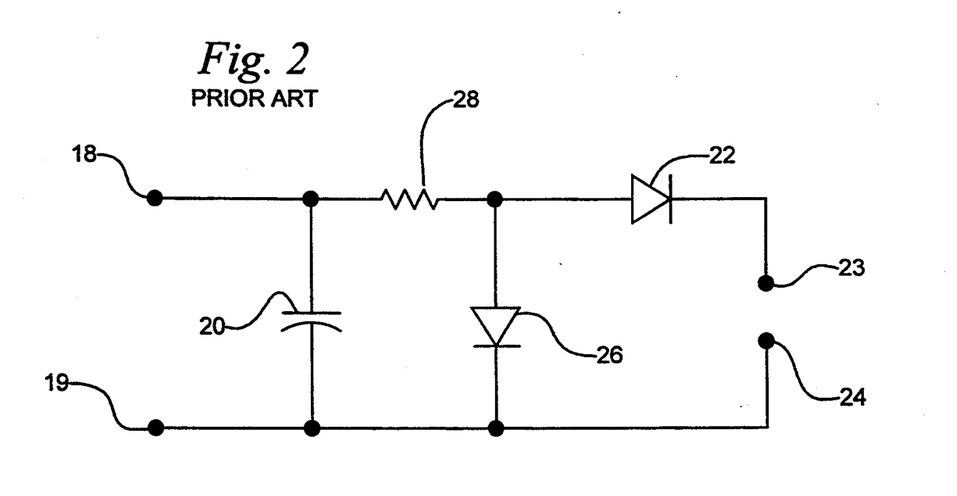
FIG. 2 is a simplified schematic diagram of a typical prior art ICD to deliver a monophasic discharge pulse.

FIG. 2 depicts this conventional mono-phasic waveform countershock 10 has traditionally been generated. After charging capacitor 20 via high voltage power source leads 18 and 19, the defibrillation countershock pulse is delivered to the myocardium through discharge leads 23 and 24 by enabling silicon controlled rectifier (SCR) 22. After six milliseconds of discharge through myocardial leads 23 and 24, SCR 26 is enabled, allowing rapid discharge of capacitor 20 through the low resistance in resistor 28 starving SCR 22 of current and turning off SCR 22.

Figure 3A:
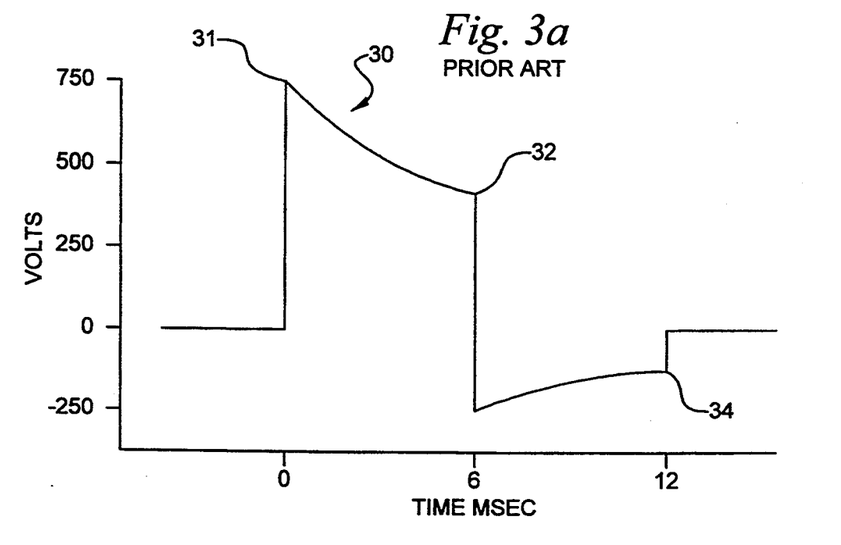
FIG. 3a is a graphic depiction of a bi-phasic voltage output of a typical prior art ICD system.

Continued research in the area of countershock therapy for ventricular fibrillation revealed that a bi-phasic waveform countershock 30, as depicted in FIG. 3, was superior to the traditional monophasic countershock 10. Leading edge voltage 31 is 750 V with a peak initial instantaneous current of 15 amps (A). At phase reversal 32 the voltage across the myocardial leads reverses from 337 V to −337 V. Total energy delivered up to phase reversal 32 is 33.6 J. Trailing edge voltage 34 is −151 V at the time of truncation 12 msec after the countershock was initiated. Total energy delivered during the 12 msec is 40.5 J.

Figure 3B:
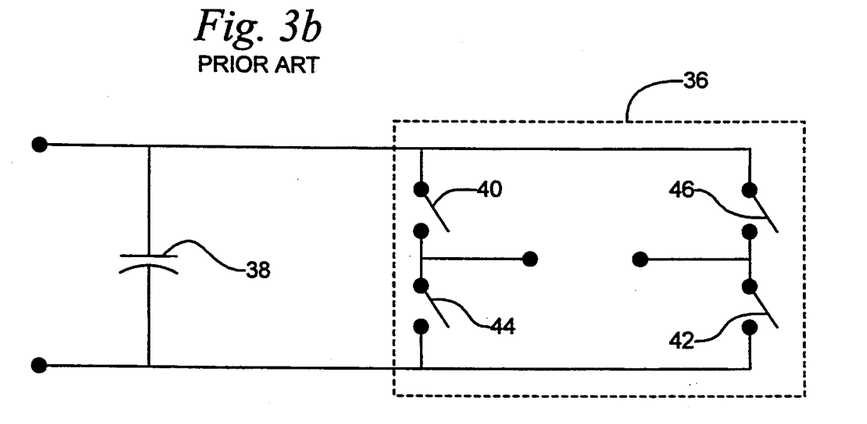
FIG. 3b is a simplified schematic diagram of a typical prior art ICD with a conventional H-bridge circuit to deliver a bi-phasic discharge pulse.

The polarity reversal creating the bi-phasic waveform is thought to serve as a source of electrical "healing" of the myocardial cell membranes and associated membrane phospholipids stressed during the first phase of the defibrillation countershock. Conventional H-bridge switching circuitry 36, as shown in FIG. 3b, may be used to generate a bi-phasic waveform. High voltage capacitor 38 discharges in the "forward" direction through the myocardium by closing switches 40 and 42 as in the traditional mono-phasic mode. At a predetermined period of time, for example the six millisecond period, switches 40 and 42 are opened and switches 44 and 46 are closed which "reverses" the current from the capacitor through the myocardium. Finally, the second phase of the bi-phasic pulse is truncated in time by opening switches 44 and 46 to complete the defibrillation countershock pulse.

Occasionally discharge electrodes from an ICD will encounter extremely low resistances across the myocardium. Resistances as low as 15 $\Omega$ have been measured after the ICD has been implanted. In such a case, depicted in FIG. 4, if the ICD is called upon to defibrillate the heart, initial instantaneous peak current 48 of 50 A would be generated (750 V/50 $\Omega$ = 50 A). This high degree of peak current has been known to cause localized permanent damage to the myocardium in the area of the electrodes. Such excess current also causes temporary "stunning" in the adjacent tissue. This temporary stunning decreases the efficacy of defibrillation countershocks because stunned cells may independently re-initiate fibrillation 100–200 milliseconds later.

An inter-electrode myocardial tissue resistance of 30 $\Omega$ still leads to initial peak currents of 25 A at 750 V of charge on the capacitor (750 V/30 $\Omega$ = 25 A). Even this current is at the border of acceptable levels, beyond which the incidence of permanent myocardial cell damage secondary to excessive peak currents goes up. Presently the only way to counter low resistance conditions is to program the ICD to charge the high voltage capacitor to a lower voltage in order to avoid the initial high peak current. However, at 15 $\Omega$ a charged voltage of just 450 V will still give an unacceptable initial peak current of 30 A (450 V/15 $\Omega$ = 30 A). Additionally, this charge will only yield 15 J total defibrillation discharge energy, an amount generally felt to be inefficacious for consistent successful defibrillation countershock therapy.

Unfortunately, the low resistance is not always present at the time of implantation. If the resistance drops later and the low resistance condition goes undetected, the patient is at risk of receiving inordinately large peak currents if the system is called upon to deliver a defibrillation countershock therapy. For additional background on fluctuating interelectrode myocardial tissue resistance, reference is made to Schwartzman, David, M.D., et. al. in *Pacing And Clinical Electrophysiology*, cited above.

Figure 4:
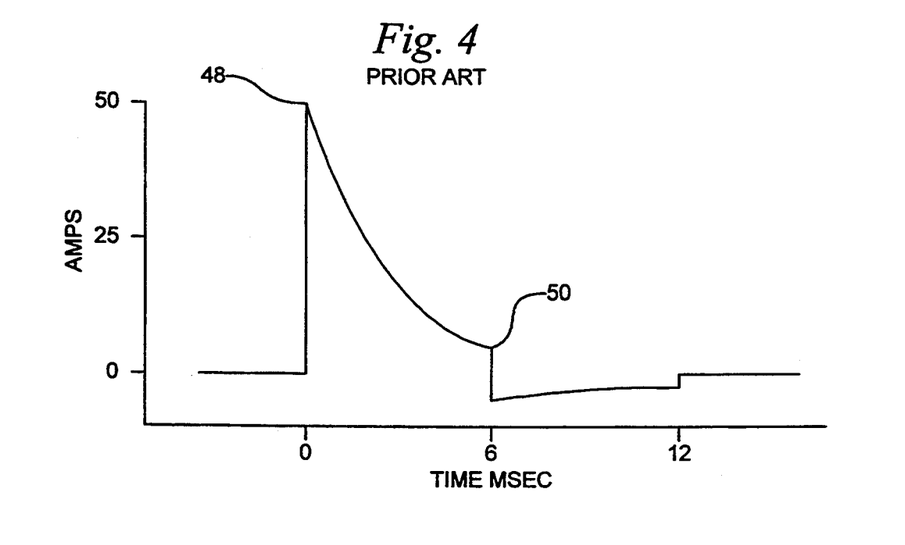
FIG. 4 is a graphic depiction of the bi-phasic current output of a typical prior art ICD system when the trans-myocardial resistance between the discharge electrodes has dropped to 15 $\Omega$.

An additional, undesirable effect of low resistance is the significantly reduced trailing voltage for the second phase of the bi-phasic defibrillation countershock pulse. As depicted in FIG. 4, using 15 Ω as the inter-electrode myocardial tissue resistance, at phase reversal 50 current has dropped to 3.5 A which corresponds to a remaining voltage of 52 V. Total energy delivered at phase reversal 50 is 42 J leaving only 0.2 J left to complete the second "reversed" phase. This will decrease, if not actually eliminate the efficacy of the "reversed" half of the bi-phasic defibrillation countershock pulse.

In summary, there are many problems created by high peak currents due to low resistance, including increased permanent cell damage, cellular stunning, and decreased ability to reverse these effects. Lowering the charging voltage in an effort to mitigate the damaging effects of low resistance leads to lowered treatment efficacy.

Figure 5:
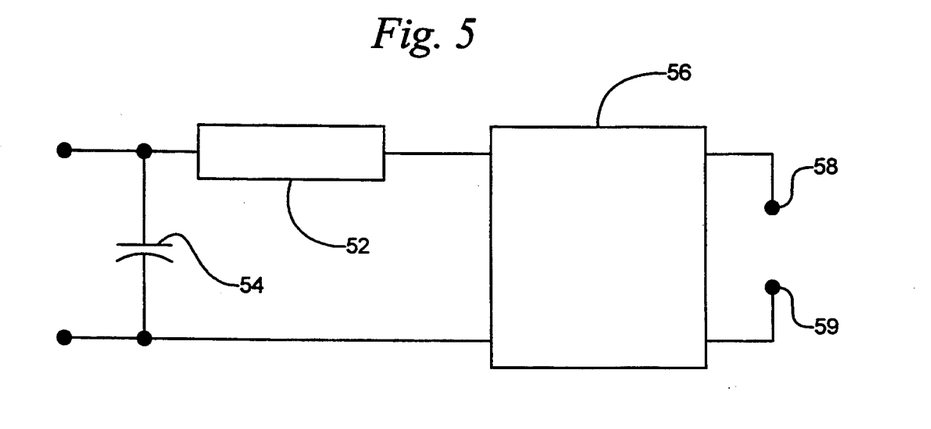
FIG. 5 is a simplified schematic diagram of an embodiment of the present invention in the output circuit of an ICD system.

The present invention provides a current truncating system and related method which when used in conjunction with automatic implantable cardioverter defibrillators forms an improved integrated system for carrying out cardiac defibrillation countershock treatment. FIG. 5 is a depiction of the output section of an ICD system modified by the present invention to include a non-linear output current truncater 52 electrically connected in series with high voltage capacitor 54 and waveform switching circuit 56 to discharge electrodes 58 and 59.

Figure 6:
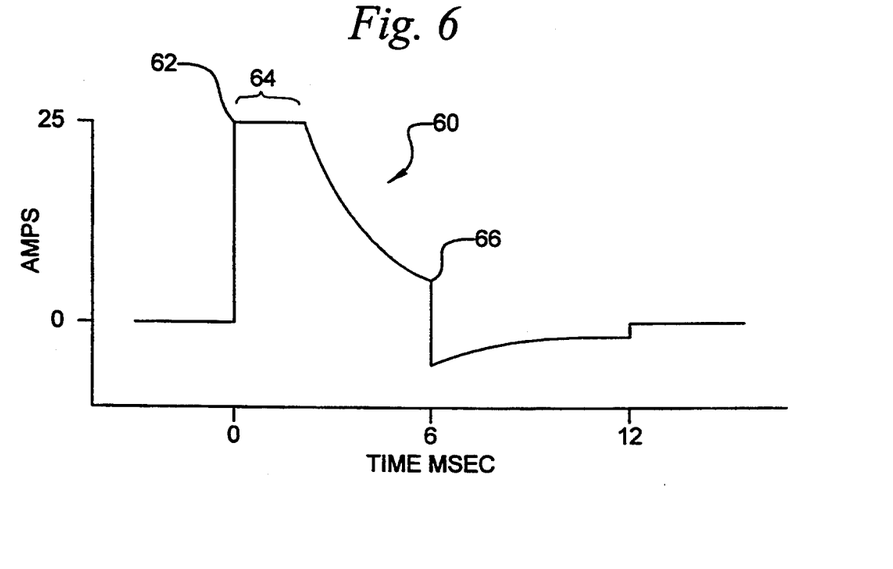
FIG. 6 is a graphic depiction of a bi-phasic current output of an embodiment of the present invention when trans-myocardial resistance between the discharge electrodes has dropped to 15 $\Omega$.

Referring to FIG. 6, under the same low resistance conditions used in FIG. 4, truncated countershock 60 has leading edge current 62 that has been truncated to a maximum of 25 A by non-linear output current truncater 52. The present invention allows for versatility in choosing any truncation parameter, but 25 A may be considered the maximum allowable before significant tissue destruction is seen. As handled by the present invention, the current remains limited during time period 64 until high voltage capacitor 54, as shown in FIG. 5, has discharged sufficiently to no longer sustain a 25 A output. At the end of time period 64 the output current begins to decay along the exponential curve typical for the capacitor used, in this case a capacitance system of two 300 μF capacitors in series, yielding an effective capacitance of 150 μF with an effective load of 15 Ω.

An additional benefit of the present invention is seen at phase reversal 66 such that truncation of the output has conserved some additional charge on capacitor 54 as compared with the charge left at phase reversal 50 for the low resistance non-truncated system depicted in FIG. 4. This additional remaining charge is available for the reversed phase of a bi-phasic defibrillation countershock pulse improving the efficacy of this second phase.

Figure 7:
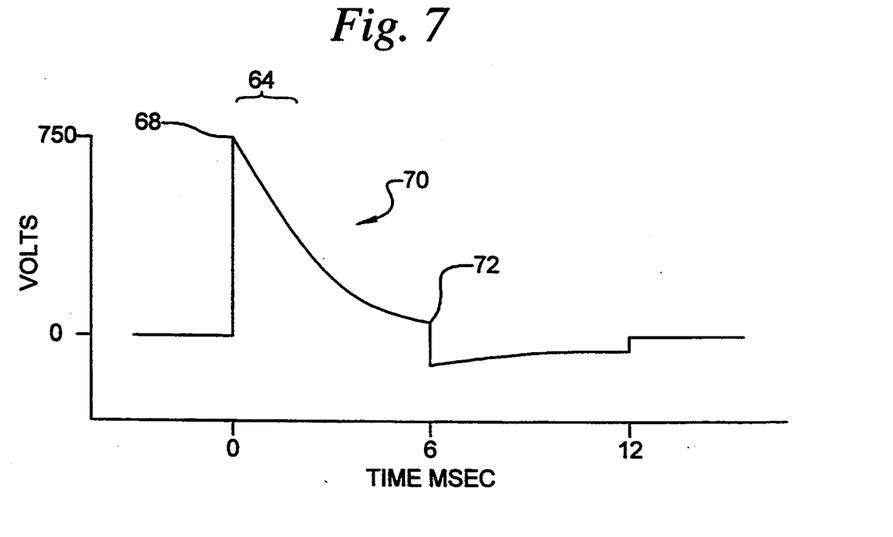
FIG. 7 is a graphic depiction of a bi-phasic voltage output of an embodiment of the present invention when trans-myocardial resistance between the discharge electrodes has dropped to 15 $\Omega$.

FIG. 7 depicts the voltage decay corresponding to the current changes shown in FIG. 6. During time period 64 the voltage decays in a linear fashion beginning at leading edge 68 to point 70 on the curve corresponding to the end of time period 64. The corresponding voltage drop is from 750 volts beginning at leading edge 68 to 375 volts at point 70. At phase reversal 72 there remains 66.3 volts of charge on a capacitor 54 which is available for the reversed second phase.

Figure 8:
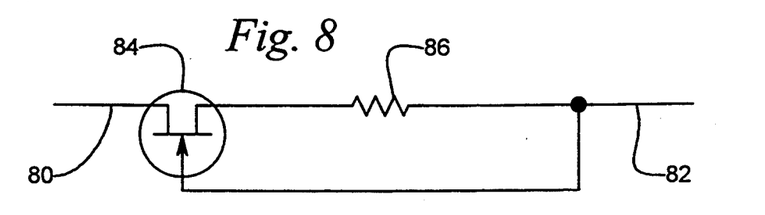
FIG. 8 is a more detailed schematic diagram of a circuit embodiment of the present invention.

FIGS. 8, 9, 10, and 11 depict schematic diagram disclosures of four different embodiments of non-linear output current truncater 52 of FIG. 5. In all four figures lead 80 is electrically connected to high voltage capacitor 54 and lead 82 is electrically connected to waveform switching circuit 56. In FIG. 8, output current truncation is accomplished by uni-junctional field effect transistor (FET) 84 and is connected in series with resistor 86. Lead 80 from high voltage capacitor 54 is connected to the drain of FET 84. The source of FET 84 is connected to resistor 86 which is then electrically connected in series to the gate of FET 84 and waveform switching circuit 56 to complete the circuit. By choosing appropriate values for resistor 86 and power rating of FET 84 an appropriate back biasing value will be placed on the gate of FET 84 creating a clamping effect on the drain current of FET 84 truncating its peak current output to 25 amps.

Figure 9:
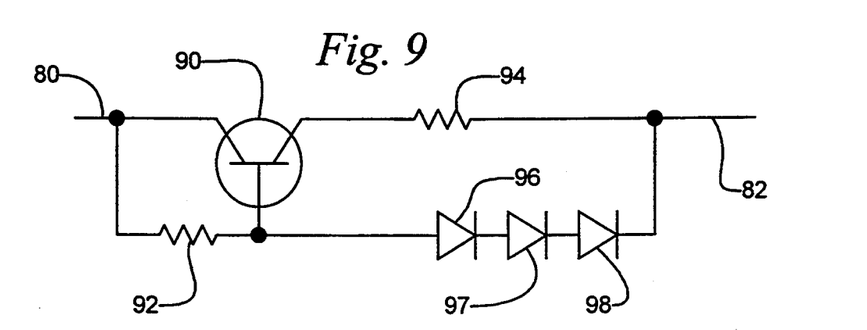
FIG. 9 is a more detailed schematic diagram of an additional circuit embodiment of the present invention.

FIG. 9 can accomplish current truncation utilizing bipolar transistor 90 which has its collector connected to lead 80 from high voltage capacitor 54. Resistor 92 is connected across the collector and base of transistor 90. The emitter of transistor 90 is electrically connected in series with resistor 94 to lead 82. The circuit is completed by connecting in series diodes 96, 97, and 98 from the base of transistor 90 to lead 82.. Values for resistors 92 and 94 are chosen such that the back biasing voltage to the base of transistor 90 is appropriate to truncate collector current flow to 25 amps or less. The three diodes 96, 97, and 98 connected in series provide the voltage potential to the base of transistor 90, but limit the voltage allowed across resister 94, hence truncating the emitter-base current.

Figure 10:
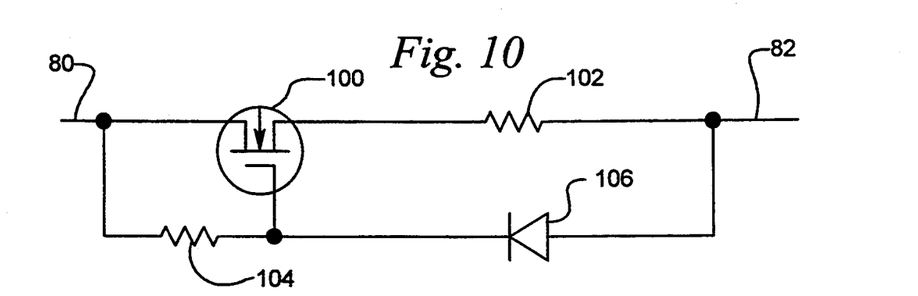
FIG. 10 is a more detailed schematic diagram of another circuit embodiment of the present invention.

The embodiment depicted in FIG. 10 utilizes metal oxide semiconductor field effect transistor (MOSFET) 100 which has its drain electrically connected to lead 80 from high voltage capacitor 54. The source of MOSFET 100 is electrically connected in series with resistor 102 to lead 82. The insulated gate of MOSFET 100 is electrically connected in series with resistor 104 to lead 80 and in series with Zener diode 106 to lead 82 from waveform switching circuit 56. The voltage control characteristics created by the series connection of Zener diode 106 and resistor 104 provides uniform voltage at the gate of MOSFET 100. Resistor 102 is of sufficiently low value to allow the bulk of the current through resistor 102 but maintain a bias voltage across the gate of MOSFET 100 such that the back biasing of the gate to MOSFET 100 will provide sufficient clamping to truncate drain current to 25 amps.

Figure 11:
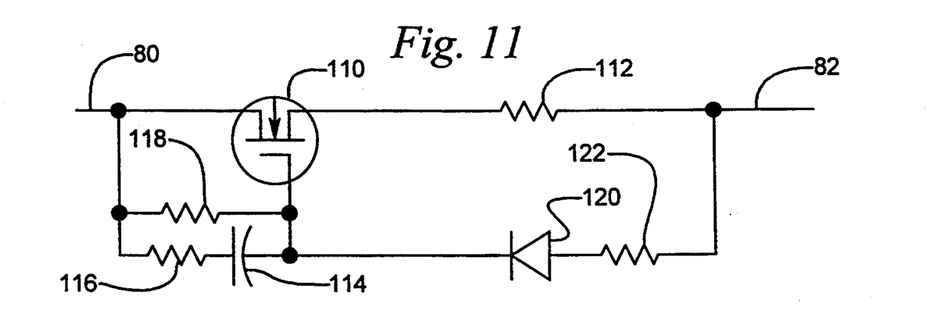
FIG. 11 is a more detailed schematic diagram of another additional circuit embodiment of the present invention.

The additional embodiment in FIG. 11 makes use of an alternative configuration utilizing the characteristics of a field effect transistor. The drain of MOSFET 110 is connected electrically to lead 80 from high voltage capacitor 54. The source of MOSFET 110 is connected electrically in series with resistor 112 to lead 82 from waveform switching circuit 56. The gate of MOSFET 110 is connected in series with capacitor 114 to resistor 116 which has its other end connected to lead 80. Additionally, resistor 118 is connected in parallel to capacitor 114 and resistor 116 from the gate of MOSFET 110 to lead 80. The circuit is completed with the electrical connection from the gate of MOSFET 110 connection in series with Zener diode 120 and resistor 122 which has its other end connected to lead 82. Once again, it is the voltage control characteristics of Zener diode 120 that maintains the bias voltage across the gate of MOSFET 110 providing current clamping, truncating the drain current to 25 A. Resistors 116 and 118 in conjunction with capacitor 114 are of appropriate values to further limit the current to a lower level after a time period related to the time constant for resistors 116 and capacitor 114 to prevent overheating of MOSFET 110.

The present invention improves upon all ICD systems which generate countershock pulses capable of generating high peak current output. The present invention does not rely on detection of low resistant conditions between implanted discharge electrodes to effect current truncation. Rather the present invention discloses a system and method that truncates peak current output to a safer level regardless of inter-electrode resistance. Because it is the excessive peak current that leads to tissue destruction and cellular stunning, efficacy is increased directly by truncating peak current. Because low resistance conditions lead to rapid power drain of the capacitance discharge, a secondary effect of excessively high initial peak current is lack of any residual energy for an effective second phase of a bi-phasic defibrillation countershock pulse. The added efficacy of bi-phasic therapy is lost. The present invention, through current truncation of initial peak current conserves energy within the capacitance power source which continues to be available to the system improving the energy output of the second phase.

Although the present invention has been described with reference to several particular embodiments, it is to be understood that these embodiments are merely illustrative of the application of the principles of the present invention. Numerous modifications and other arrangements may be devised without departing from the spirit and scope of the invention.

We claim:

1. A method for operating an implantable device electrically connected to two or more implanted discharge electrodes located in a human patient to treat a myocardial fibrillation, the method comprising the device-implemented steps of:
    (a) sensing a myocardial fibrillation in the human patient; and
    (b) in response to the myocardial fibrillation,
        (b1) charging a charge storage system to a voltage;
        (b2) discharging a current from the charge storage system through the two or more implanted electrodes to generate a defibrillation countershock; and
        (b3) truncating the discharge of the current to truncate a peak current of the defibrillation countershock to less than a predetermined amount regardless of an effective resistance value into which the defibrillation countershock is discharged.

2. The method of claim 1 in which the predetermined amount is less than about 40 Amperes.

3. The method of claim 1 in which the predetermined amount is less than about 30 Amperes.

4. The method of claim 1 in which, the predetermined amount is less than about 25 Amperes.

5. The method of claim 1 in which the predetermined amount is less than about 20 Amperes.

6. An implantable cardioverter defibrillator apparatus, the implantable cardioverter defibrillator apparatus being a self-contained human implantable device for treating cardiac arrhythmias that is electrically connected to at least two implanted discharge electrodes located in a human patient, the at least two implanted discharge electrodes having an effective resistance that is variable dependent upon the at least two implanted electrodes defining a discharge pathway therebetween and a physiological condition of the human patient across the discharge pathway, the apparatus comprising:
    (a) storage means electrically connected to the two or more implanted electrodes for storing an electrical charge to be delivered to the two or more implanted electrodes;
    (b) sensing means for sensing a cardiac arrhythmia in the human patient;
    (c) power source means for charging the storage means to a voltage; and
    (d) discharge means for selectively discharging the storage means in response to the sensing of the cardiac arrhythmias to deliver the electrical charge as a countershock that is current truncated such that the countershock has a peak current less than a predetermined amount regardless of the effective resistance value of a discharge pathway into which the countershock is delivered.

7. The system of claim 6 in which the discharge means comprises a non-linear current truncation means electrically connected in series between the capacitor means and the two or more discharge electrodes.

8. The system of claim 7 further comprising a waveform switching means electrically connected in series between the non-linear current truncation means and the two or more discharge electrodes for providing multiple waveforms of the defibrillation countershock.

9. The system of claim 7 in which the non-linear current truncation means includes a uni-junctional field effect transistor having a drain, a source, and a gate in which:
    the drain is electrically connected to the storage means;
    the source is electrically connected in series with a resistor to the gate; and
    the gate is electrically connected to the two or more discharge electrodes.

10. The system of claim 7 in which the non-linear current truncation means includes a bipolar transistor having a collector, an emitter and a base in which:
    the collector is electrically connected to the storage means;
    the emitter is electrically connected in series to the base, the electrical connection commencing from emitter to base comprising a first resistor connected to a series of two or more diodes and the discharge electrodes being electrically connected between the first resistor and the series of two or more diodes; and
    the base is electrically connected in series to the collector with a second resistor.

11. The system of claim 7 in which the non-linear current truncation means includes a metal oxide semiconductor field effect transistor having a drain, a source and a gate in which:

the drain is electrically connected to the storage means;

the source is electrically connected in series to the gate, the electrical connection commencing from source to gate comprising a first resister connected to a Zener diode and the discharge electrodes being electrically connected between the first resistor and the Zener diode; and the gate is electrically connected in series to the drain with a second resistor.

12. The system of claim 7 in which the non-linear current truncation means includes a metal oxide semiconductor field effect transistor having a drain, a source and a gate in which: the drain is electrically connected to the storage means; the source is electrically connected in series to the gate, the electrical connection commencing from source to gate comprising a first resistor connected to a second resistor connected to a Zener diode and having the discharge electrodes being electrically connected between the first and second resistors; and the gate is electrically connected to the drain, the electrical connection commencing from gate to drain comprising a first connection being a series circuit having a capacitor connected in series with a third resistor and a second connection with a fourth resistor in parallel to the first connection.

13. The system of claim 6 in which the predetermined amount is less than about 40 Amperes.

14. The system of claim 6 in which the predetermined amount is less than about 30 Amperes.

15. The system of claim 6 in which the predetermined amount is less than about 25 Amperes.

16. The system of claim 6 in which the predetermined amount is less than about 20 Amperes.

* * * * *